United States Patent [19]
Bill et al.

[11] Patent Number: 5,241,083
[45] Date of Patent: Aug. 31, 1993

[54] PROCESS FOR CONVERTING THE 13-α-HYDROXY GROUP OF AVERMECTIN AGLYCONES

[75] Inventors: Timothy Bill, Williamsburg, Va.; Chris H. Senanayake, North Brunswick, N.J.; Robert D. Larsen, Bridgewater, N.J.; Sheo B. Singh, Edison, N.J.; Thomas R. Vernhoeven, Cranford, N.J.

[73] Assignee: Merck & Co., Inc., Rahway, N.J.

[21] Appl. No.: 907,429

[22] Filed: Jul. 1, 1992

[51] Int. Cl.$^5$ .................................. C07D 313/00
[52] U.S. Cl. ..................................... 549/264
[58] Field of Search ............................. 549/264

[56] References Cited

U.S. PATENT DOCUMENTS

| | | | |
|---|---|---|---|
| 4,199,569 | 4/1980 | Chabala et al. | 424/180 |
| 4,310,519 | 1/1982 | Albers-Schonberg et al. | 424/181 |
| 4,895,837 | 1/1990 | Mrozik et al. | 514/30 |
| 4,906,619 | 3/1990 | Eskola et al. | 514/30 |

FOREIGN PATENT DOCUMENTS 0007812 2/1980 European Pat. Off.
0214731 3/1987 European Pat. Off.

OTHER PUBLICATIONS

Cainelli et al., Tetrahedron, 41: 1385–1392 (1985).
Hughes et al., J. Am. Chem., 110: 6487–6491 (1988).
Mitsunobu, Synthesis, pp. 1–28 (1981).
Mrozik et al., J. Med. Chem., 32: 375–381 (1989).

Primary Examiner—C. Warren Ivy
Assistant Examiner—Ba K. Trinh
Attorney, Agent, or Firm—Sylvia A. Ayler; Mark R. Daniel; Joseph F. DiPrima

[57] ABSTRACT

The natural stereochemistry at the 13-position of avermectin aglycones, normally α-oriented or below the plane of the molecule, is inverted or epimerized into the β-position. The procedure starts with the avermectin aglycone compounds where the 13α-hydroxy group is activated to a mesylate leaving group. The resultant 13-α-mesylate is then displaced with a cesium carboxylate and one equivalent of the respective carboxylic acid, ending with the ester group being converted to the 13-β-hydroxy configuration by transesterification in high yield.

7 Claims, No Drawings

PROCESS FOR CONVERTING THE 13-α-HYDROXY GROUP OF AVERMECTIN AGLYCONES

BACKGROUND OF THE INVENTION

Avermectin compounds are well known antiparasitic agents useful in animal health, human health and agriculture. The avermectin compounds, and the related milbemycin compounds are prepared micro-biologically and are highly complex organic molecules. See Albers-Schoenberg et al, U.S. Pat. No. 4,310,519 and Chabala et al, U.S. Pat. No. 4,199,569. Avermectin B1 is composed of a mixture, typically 80% a and 20%, of the 25-sec-butyl (B1a) and 25-isopropyl (B1b) side chains. Thoughout the specification avermectin B1 will refer to this mixture. The minor structural difference has been found to have very little effect on the chemical reactivity or biological activity of the compounds. The natural stereochemistry of the 13-position substituent of the avermectins is α, with the oxygen atom below the plane of the ring.

Inversion of the 13-position from the α to the β configuration produces a highly desirable functionality, useful in the preparation of 13-epi compounds and active as anthelmintic agents. Prior efforts at inverting the 13-position stereochemistry were complex, multi-step syntheses that resulted in poor yields and mixtures of isomers. See Mrozik et al, *J. Med. Chem.*, 32 pg 375–381 (1989). Pending U.S. patent application Ser. No. 698,874, filed May 13, 1991, describes a process for preparing 13-β-compounds whereby a 13-α leaving group is displaced by tetraalkylammonium nitrate followed by reduction of the resultant nitrate ester with zinc in the presence of acid to yield the 13-β configuration. However, this process employs expensive reagents that are not readily available and conversion to the nitrate ester is low. Additionally, reduction of the nitrate ester is a difficult process not amenable to scale up. Efforts at preparing the 13-β compounds also have not been successful when traditional epimerization procedures were attempted such as the well-known Mitsunobu inversion reaction. See Mitsunobu, *Synthesis* pg 1–28 (1981) and Hughes et al, *J. Am. Chem. Soc.*, 110 pg 6487–6491 (1988). See also Cainelli et al, *Tetrahedron Lett.* 26 pg 3369–3372 (1985) and Cainelli et al, *Tetrahedron* 41 pg 1385–1892 (1985) for a general description of an inversion process involving nucleophilic displacement promoted by nitrate ions. Of all of the procedures attempted, the inversion of the 13-position stereochemistry is most readily accomplished as described below with the highest yields of any such processes.

SUMMARY OF THE INVENTION

The instant invention is concerned with a procedure for the inversion of the 13-position stereochemistry of the compounds. Thus, it is an object of the instant invention to describe a process for the efficient preparation of avermectin aglycone compounds with inverted 13-position stereochemistry. A further object is to describe the specific reaction conditions which most efficiently produce the stereochemically inverted compounds. A still further object is to describe the intermediates used in the inversion process. Still further objects will become apparent from a reading of the following description.

DESCRIPTION OF THE INVENTION

The process of inverting the natural α-stereochemistry of the avermectin aglycone 13-position hydroxy into the inverted or β-configuration, also sometimes referred to as 13-epi-aglycones, is outlined in the following reaction scheme.

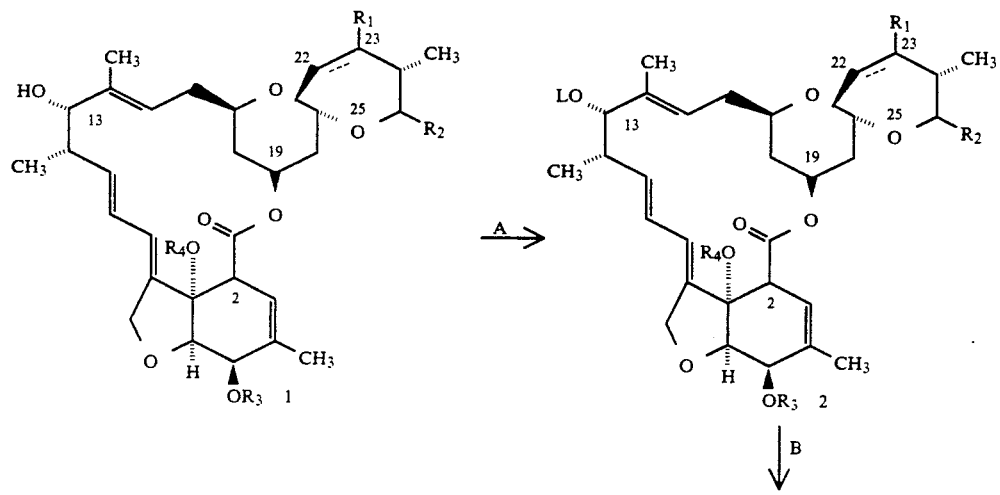

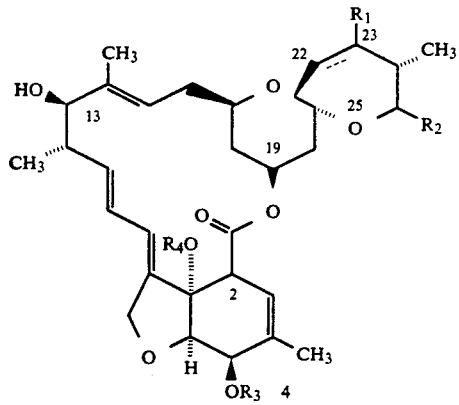 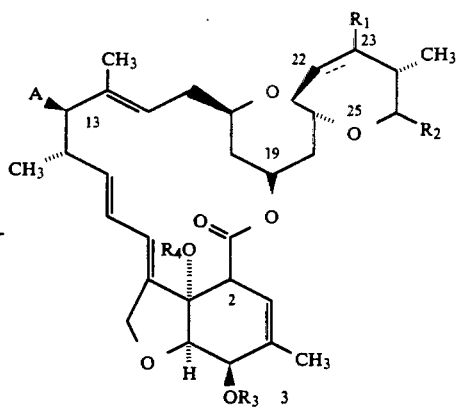

where
L is a leaving group and the broken line at the 22,23-position indicates either a single or a double bond at the 22,23-position;
R₁ is present only when the broken line indicates a 22,23-single bond and is hydrogen, hydroxy, or oxo;
R₂ is loweralkyl, loweralkenyl, or cyclololweralkyl;
A is an alkanoate;
R₃ is tert-butyldimethylsilyl; and
R₄ is trimethylsilyl.

In the instant application, the following terms are intended to have the following definitions:

The term "loweralkyl" is intended to include those alkyl groups containing from 1 to 6 carbon atoms in either a straight or branched configuration. Examples of such alkyl groups are methyl, ethyl, n-propyl, isopropyl, n-butyl, sec-butyl, isobutyl, tert-butyl, n-pentyl, iso-pentyl, neo-pentyl, n-hexyl, iso-hexyl and the like.

The term "loweralkenyl" is intended to include those alkenyl groups of from 2 to 6 carbon atoms in either a straight or branched configuration. Examples of such alkenyl groups are ethenyl, 1-propenyl, 2-propenyl, 1-butenyl, 2-butenyl, 1-pentenyl, 4-methyl-2-penten-2-yl, 3-pentenyl, 1-hexenyl, 2-hexenyl and the like.

The term "cycloalkyl" is intended to include those cycloalkyl groups of from 3 to 8 carbon atoms. Examples of such cycloalkyl groups are cyclopropyl, cyclobutyl, cyclopentyl, cyclohexyl, cycloheptyl and cyclooctyl.

The term "alkonoate" is intended to include those alkanoate groups of from 2 to 10 carbon atoms in either a straight or branched configuration. Examples of such groups are propionate, ethanoate, methoxyacetate, benzoate, deconoate and the like.

The instant invention also includes the intermediate carboxy compounds, 3 above, both as intermediates in the preparation of 13-epi compounds and as active anthelmintic agents themselves. The compounds in the above structural formula are of the embodiment wherein the broken line indicates a 22,23-single bond and
R₁ is hydrogen, hydroxy or oxo;
R₂ is alkyl of from 3 to 5 carbon atoms or cycloalkyl of from 4 to 6 carbon atoms;
R₃ is tert-butyldimethylsilyl; and
R₄ is trimethylsilyl.

A subclass of the embodiment is realized when
R₁ is hydrogen or oxo;
R₂ is alkyl of 3 to 4 carbon atoms or cycloalkyl of 5 to 6 carbon atoms; and
R₃ is tert-butyldimethylsilyl; and
R₄ is trimethylsilyl.

Still a further subclass of the embodiment is realized when
R₁ is hydrogen;
R₂ is isopropyl, sec-butyl, cyclohexyl or cyclopentyl; and
R₃ is tert-butyldimethylsilyl; and
R₄ is trimethylsilyl.

The preparation of derivatives of avermectin aglycone compounds which are used as the starting materials for the instant process are well described in the scientific and patent literature. See, for example U.S. Pat. No. 4,310,519 to Albers-Schoenberg et al, for the avermectin natural products; U.S. Pat. No. 4,199,569 to Chabala et al, for the 22,23-dihydroavermectin derivates; U.S. Pat. No. 4,906,619 to Eskola et al, for the preparation of various alkylated avermectins; U.S. Pat. No. 4,200,981 to Fisher et al, for the preparation of various 5-alkylated compounds; U.S. Pat. No. 4,895,837 to Mrozik for a discussion of various procedures for the protection of avermectin compounds; European Patent application 214,731 for the preparation of various 25-alkyl, alkenyl and cycloalkyl derivatives; see also Chen et al, *Abstr. Pap. Am. Chem. Soc.*, (186 Mtg MBTD 28 (1983)) for additional 25-substituted compounds; and Fisher et al, in *Macrolide Antibiotics*, Omura, S (ed), Academic Press, New York and Davies et al, in *Nat. Prod. Rep.* 3 pg 87–121 (1986) reviews the literature of avermectin and milbemycin compounds for the preparation of additional compounds.

The process for the inversion of the 13-position stereochemistry from α- to β-begins with the avermectin aglycone compound with a free 13-hydroxy group and any additional hydroxy groups, such as those at the 5, 7 and 23-positions, protected to prevent reactions at those positions. It is noted that the 7-position hydroxy group is generally reactive under the reaction conditions employed in the instant series of reactions and is therefore protected to provide higher yields.

Subsequent to any of the above described reactions the protecting group may be removed and the unprotected product isolated. The protecting group employed is ideally one which may be readily synthesized, will not be affected by the reactions at the other positions and may be readily removed without affecting any other functions of the molecule. One preferred type of protecting group for the avermectin type of molecule is the tri-substituted silyl group, preferably the trialkylsilyl group. One especially preferred example, is the t-butyl dimethylsilyl group. The reaction preparing the protected compounds is carried out by reacting the hydroxy compounds with the appropriately substituted silylhalide, preferably the silylchloride in an aprotic polar solvent such as dimethylformamide, tetrahydrofuran, etc.,. Imidazole is added as a base. The reaction is complete in from 1 to 24 hours and at from 0° to 25° C. For the 5-position hydroxy group the reaction is complete in from ½ to 3 hours at from 0° C. to 50° C. This reaction is selective to the 5-position under the conditions above described and very little, if any, silylation is observed at other hydroxy substituted positions. If it is desired to protect the 23-hydroxy group a 5,23-di(-phenoxyacetyl) derivative or a 23-silyl ether can be prepared. Basic hydrolysis will leave the highly hindered 23-0-substituent but hydrolyze the 5-0-phenoxy acetyl groups. The 5-position is then protected as described above, selectively with a t-butyldimethylsilyl group.

The silyl group or groups are removed by stirring the silyl compound in methanol catalyzed by an acid preferably a sulfonic acid hydrate such as methanolic 1.0% p-toluene sulfonic acid monohydrate. The reaction is complete in about 1 to 12 hours at from 0° to 50° C. Alternatively the silyl group or groups may be removed by treatment of the silyl compound with anhydrous pyridine-hydrogen fluoride in acetonitrile. The reaction is complete in from 3 to 24 hours at from 0° to 25° C.

The first step in the inversion of the 13-position stereochemistry involves the substitution of a leaving group (L) on the suitably protected 13-hydroxy compound, Step A. The nature of the leaving group is not significant so long as it can be readily substituted on Compound 1 at the 13-hydroxy position and is readily displaced in Step B of the instant process. Preferred leaving groups are sulfonyl derivatives with the methanesulfonyl derivative (mesylate) most preferred. Mesylation is enhanced with the use of a base mixture of diisopropylethylamine and dimethylaminopyridine without the occurence of any side reactions such as displacement by chloride, which lowers yield. The typical conditions for mesylation (methanesulfonyl chloride-triethylamine) give complex product mixtures along with the desired product.

Substitution is conducted by dissolving compound 1 above in a non-polar solvent such as a chlorinated hydrocarbon preferably chloroform or methylene chloride and cooling from −20° C. to −15° C. Dimethylaminopyridine and diisopropylethylamine are then added to the solution and mixed at about −20° C. to −15° C. for about from 10 minutes to 1 hour with the addition of methanesulfonyl chloride while the internal temperature is maintained at about from −15° C. to −2° C. The reaction is generally complete in from ½ to 10 hours and the product, Compound 2, is isolated using techniques known to those skilled in the art.

The second step, Step B, of the reaction sequence involves inversion of the 13-position stereochemistry with the simultaneous displacement of the leaving group by a cesium carboxylate such as cesium pentanoate, cesium decanoate, cesium methoxy acetate, cesium acetate or cesium propionate, cesium propionate and cesium acetate most preferred, in the presence of 18-Crown-6 and an equivalent of the respective carboxylic acid. Cesium propionate is prepared from cesium carbonate and propionic acid by methods known to those skilled in the art. Addition of an equivalent of the respective carboxylic acid has been found to significantly promote displacement, giving unexpected high yields and minimal byproduct formation.

The reaction is carried out in an inert solvent, preferably a non-polar solvent such as a hydrocarbon such as benzene, toluene and the like. Toluene is preferred. The reaction is run at from 90° C. to 115° C. and is complete in from 2 hours to 8 hours. The 13-epi carboxyl substituted hydroxy compound (Compound 3) is isolated using techniques known to those skilled in the art.

The carboxy substituted group is then converted in Step C to a 13-β-OH without again inverting the 13-position stereochemistry by metal-mediated transesterification/reduction. The transesterification/reduction is catalyzed by metal oxides and hydrides such as titanium isopropoxide and lithium aluminum hydride, titanium isopropoxide most preferred. The reaction is carried out at about 70° C. to 80° C., in an alcoholic solvent, such as ethanol, isopropanol and the like, in which Compound 3 is soluble or slightly soluble.

The following examples are provided in order that this invention might be more fully understood; they are not to be construed as limitative of the invention.

General

High Performance Liquid Chromatography (HPLC) was performed on a Protein and Peptide C-18, 2.5 cm×4.6 mm column under the following conditions: column temperature −25° C., solvent—$CH_3CN:H_2O$ with 0.1% $H_3PO_4$ in each; gradient elution 90:10 to 100:0 in 30 min., flow—3.0 ml/min, wavelength—244 nm on a Spectra 100 variable wavelength dector; AUFS 0.1. Solvents for reactions were reagent grade. All reactions were performed under an inert atmosphere of dry nitrogen in dry glassware.

EXAMPLE 1

5-O-tert-Butyldimethylsilyl-7-O-trimethylsilyl-13-O-methanesulfonyl-22,23-dihydroavermectin B1 aglycone 2

In a three-necked flask fitted with an overhead stirrer under a nitrogen atmosphere 5-O-tert-butyldimethylsilyl-7-O-trimethylsilyl-22,23-dihydroavermectin B1 aglycone 1 (250 g, 323.4 mmol, 98.25% by HPLC) was dissolved in dichloromethane (1L) and the solution was cooled to −19° C. in an acetonitrile/dry ice bath. Dimethylaminopyridine (78.91 g, 646 mmol) and diisopropylethylamine (168.67 ml, 970.23 mmol) were added to the solution and the mixture was stirred at −19° C. for 10 min. Methanesulfonyl chloride (52.01 ml, 646.83 mmol) was added while the internal temperature was maintained at −2° C. (exotherm was @ 20° C). This mixture was stirred at −12° C. for 35 minutes. Hexanes (3L) was added and the reaction mixture was filtered through a silica gel pad (200 g, 230–400 mesh) to remove the base line impurities and salts which had precipitated. The filter cake was washed with hexanes (2L). The combined filtrates were added to 5% $NaHCO_3$ (1L) and this mixture was diluted with ethyl acetate (500 mL) to achieve a clean phase cut. The organic layer was washed with a 5% brine solution (0.5L) and with distilled water (2×0.5L). The organic layer was dried over magnesium sulfate (50 g), filtered and concentrated in vacuo to afford a 97% yield of 5-O-tert-butyldimethylsilyl-7-O-trimethylsilyl-13-O-methanesulfonyl-22,23-dihydroavermectin B1 aglycone (13-α- mesylate) 2 in 97.5% purity by HPLC area %, retention time: 13-α-mesylate 2 B1b, B1a-4.48, 5.17 min.; 13-α-alcohol 1 B1b, B1a-5.75, 6.55 min. $^{13}$C NMR (CDCl$_3$, 100.61 MHz) δC (ppm) 170.5, 141.6, 134.3, 134.3, 133.3, 126.0, 120.7, 120.5, 120.3, 95.6, 87.8, 83.4, 80.7, 77.5, 69.4, 68.7, 67.3, 67.0, 47.3, 41.8, 39.4, 38.9, 36.5, 35.7, 35.6, 34.4, 31.2, 28.1, 27.5, 25.9, 20.0, 19.4, 18.4, 17.5, 14.7, 12.5, 11.6, 2.4, −4.5, −4.7.

EXAMPLE 2

5-O-tert-butyldimethylsilyl-7-O-trimethylsilyl-13β-propionoxy-22,23-dihydroavermectin B1 aglycone 3

In a 1-L flak equipped with a magnetic stir bar were added cesium carbonate (3.528 g, 10.0 mmol), 18-Crown-6 (3.8 g, 11.7 mmol), toluene (240 ml) and propioinc acid (2.98 mL, 40.0 mmol). Under a nitrogen atmosphere the mixture was heated to 110° C. for 2 hours. 5-O-tert-butyldimethylsilyl-7-O-trimethylsilyl-13-O-methanesulfonyl-22,23-dihydroavermectin B1 aglycone, 2 (10 g, 11.73 mmol) in toluene (30 mL) was added and the reaction mixture was heated at 110° C. for 2.5 hours. The mixture was then cooled to 10° C. and hexanes (500 mL) was added. This mixture was filtered through a fritted funnel and the filtrate was diluted with ethyl acetate (250 mL). The combined solution was washed with a 5% NaHCO$_3$ (300 mL) and brine (300 mL). The organic layer was dried over magnesium sulfate (20.00 g), filtered and concentrated in vacuo to afford 9.3 g of crude 13-β-propionate. In a 500 mL flask the crude propionate and imidazole (5.69 g, 88.90 mmol) were dissolved in THF (140 mL) and the solution was cooled to 0° C. Under nitrogen atmosphere chlorotrimethylsilane (5.34 mL, 42 mmol) was added and the mixture was stirred at 0° C. for 10 min. The reaction mixture was then allowed to warm to room temperature and stirred for 19 hours. Hexanes (300 mL) was added and this mixture was filtred through a fritted funnel. The filtrate was washed with 5% NaHCO$_3$ (300 mL) and brine (300 mL). The organic layer was dried over sodium sulfate (50 g), filtered and concentrated in vacuo to afford 9.4 g of 5-O-tert-butyldimethylsilyl-13β-propionoxy-22,23-dihydroavermectin B1 aglycone, 3, 69% yield with a purity of greater than 96 area % by HPLC. Retention times: 13-β-propionoxy 3 B1b, B1a-9.78, 10.94 min; 13-α-mesylate 2 B1b, B1a-4.47, 5.16 min. $^{13}$C NMR (CDCl$_3$, 100.61 MHz) δC (ppm) 173.7, 170.6, 141.2, 137.0, 135.7, 134.3, 126.2, 124.5, 120.8, 120.3, 97.5, 83.6, 83.4, 80.8, 77.1, 69.4, 69.1, 67.3, 67.1, 47.3, 41.9, 39.8, 36.4, 35.65, 35.57, 34.5, 31.3, 28.1, 27.9, 27.4, 25.9, 20.0, 19.0, 18.4, 17.5, 12.5, 11.7, 11.1, 9.2, 2.3, −4.5, −4.7.

EXAMPLE 3

5-O-tert-Butyldimethylsilyl-7-O-trimethylsilyl-13-epi-22,23-dihydro-avermectin B1 aglycone 4

The 5-O-tert-butyldimethylsilyl-7-O-trimethylsilyl-13-β-propionoxy-22,23-dihydroavermectin B1 aglycone 3 (50 g, 60.34 mmol) was dissolved in isopropanol (950 mL) in a 2L round-bottomed flask fitted with a reflux condenser. To the solution under a nitrogen atmosphere was added titanium isopropoxide (56 mL, 188.13 mmol) and this mixture was heated at 80° C. for 12 hours. The reaction mixture was allowed to cool to 25° C. and was diluted with 2.5L of ethyl acetate. This solution was washed with a 2% H$_3$PO$_4$ (2.5L), 5% NaHCO$_3$ (2.5 mL), and 10% brine (2.5L). The organic layer was dried over magnesium sulfate (80 g), filtered and concentrated in vacuo to produce 45 g of crystaline 5-O-tert-butyldimethylsilyl-7-O-trimethylsilyl-13-epi-22,23-dihydroavermectin B1 aglycone 4 in greater than 95% yield with a purity of greater than 94 area % by HPLC, retention times: 13-epi-4 B1b, B1a-4.87, 5.85 min.; 13-β-propionoxy-3 B1b, B1a-10.05, 11.21 min. $^{13}$C NMR (CDCl$_3$, 100.61 MHz) δC (ppm) 170.7, 140.7, 140.2, 138.2, 134.2, 123.8, 123.7, 121.0, 120.3, 97.5, 83.7, 83.4, 80.8, 77.1, 69.4, 69.1, 67.4, 67.3, 47.3, 41.9, 41.6, 36.3, 35.6, 35.55, 34.5, 31.2, 28.1, 27.4, 25.9, 20.0, 19.3, 18.4, 17.5, 12.5, 11.7, 10.6, 2.3, −4.5, −4.7.

What is claimed is:

1. A process for the inversion of the natural α-configuration of the 13-position hydroxy group of avermectin aglycone compounds which comprises, in Step A, treating a compound having the formula:

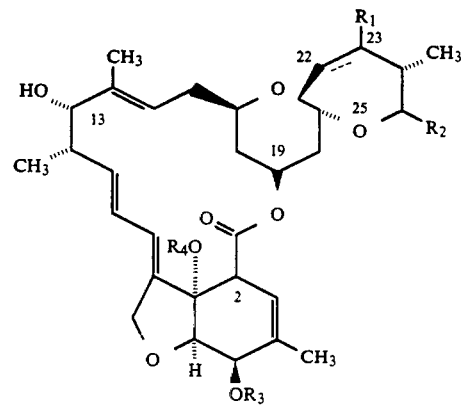

where the broken line at the 22,23-position indicates either a single or a double bond at the 22,23-position;
R$_1$ is present only when the broken line indicates a 22,23-single bond and is hydrogen, hydroxy or oxo;
R$_2$ is loweralkyl, loweralkenyl or cycloloweralkyl;
R$_3$ is tert-butyldimethylsilyl; and
R$_4$ is trimethylsilyl;
with an acylating reagent methanesulfonyl anhydride or chloride to form a compound having the formula:

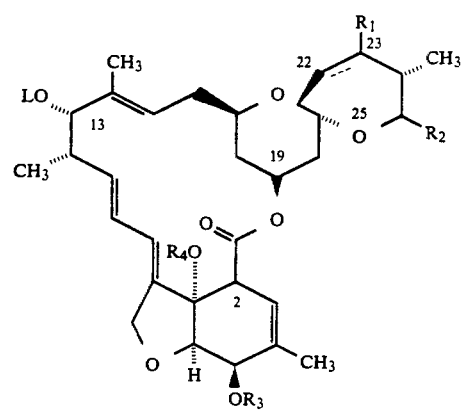

where L is a sulfonyl derivative leaving group, which is then reacted, in Step B, with a cesium carboxylate in the presence of 18-Crown-6 and an equivalent of the respective carboxylic acid to form an inverted 13-β loweralkanoate derivative of the formula:

where A is an alkanoate of from 2 to 10 carbon atoms either straight or branched configuration, which is transesterified or reduced, in Step C, with a respective metal oxide or hydride to form the 13-β-hydroxy derivative of the formula:

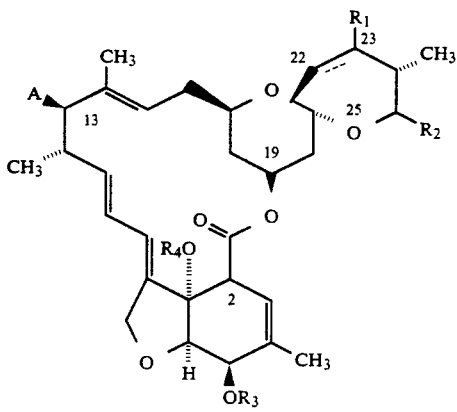

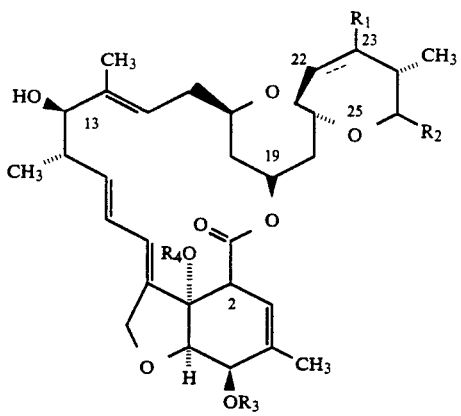

where $R_1$, $R_2$, $R_3$ and $R_4$ are as defined above.

2. The process of claim 1 where the acylating reagent in Step A is contacted with a base mixture of diisopropylethylamine and dimethylaminopyridine.

3. The process of claim 1 where the leaving group for Step A is methane sulfonate, the inversion in Step B with a cesium carboxylate occurs in the presence of 18-Crown-6 and an equivalent of the respective carboxylic acid and the transesterification or reduction medium in Step C is titanium isopropoxide or lithium aluminum hydride, respectively.

4. The process of claim 3 where the cesium carboxylate in Step B is cesium propionate or cesium acetate.

5. The process of claim 1 where
the broken line indicates a 22,23-single bond and
$R_1$ is hydrogen, hydroxy or oxo;
$R_2$ is alkyl of from 3 to 5 carbon atoms or cycloalkyl of from 4 to 6 carbon atoms;
A is propionate or acetate;
$R_3$ tert-butyldimethylsilyl; and
$R_4$ trimethylsilyl.

6. The process of claim 4 where
$R_1$ is hydrogen or oxo; and
$R_2$ is alkyl of 3 to 4 carbon atoms or cycloalkyl of 5 to 6 carbon atoms.

7. The process of claim 4 where
$R_1$ is hydrogen; and
$R_2$ is isopropyl, sec-butyl, cyclohexyl or cyclopentyl.

* * * * *